US005750896A

United States Patent [19]

Morgan et al.

[11] Patent Number: 5,750,896
[45] Date of Patent: May 12, 1998

[54] TOOL JOINT SENSOR

[75] Inventors: Felix E. Morgan; Randall S. Page; Sam D. Monaco, all of Albuquerque, N. Mex.

[73] Assignee: Hughes Aircraft Company, Los Angeles, Calif.

[21] Appl. No.: 279,368

[22] Filed: Jul. 22, 1994

[51] Int. Cl.[6] .................................................. G01N 29/24
[52] U.S. Cl. ........................................... 73/622; 73/628
[58] Field of Search ................................ 73/599.62, 622, 73/625, 632, 637, 638, 649; 364/552.56

[56] References Cited

U.S. PATENT DOCUMENTS 5,156,636  10/1992  Kuljis .................................... 73/622

Primary Examiner—Christine K. Oda
Attorney, Agent, or Firm—Leonard A. Alkov; William C. Schubert; Glenn H. Lenzen, Jr.

[57] ABSTRACT

Detection and gauging of a joint (18) in a rotating and axially moving drilling tool (16) subject to transverse axial displacement is achieved by positioning an ultrasonic sensor assembly (12) coaxially encircling the tool in a plane perpendicular to the tool. The sensor assembly (12) generates more than one reflected pulse to represent changes in tool (16) diameter by transmitting a beam from at least one ultrasonic sensor (32) toward the tool (16) as the tool axially advances or recedes, perpendicularly piercing the plane of the sensor assembly (12). Each reflected pulse is converted to an electrical output signal, all of which signals are summed to minimize measurement distortion due to noise and transverse axial displacement of the rotating tool and compared to a threshold detection voltage in a signal processor (14) to generate a detection output pulse.

25 Claims, 3 Drawing Sheets

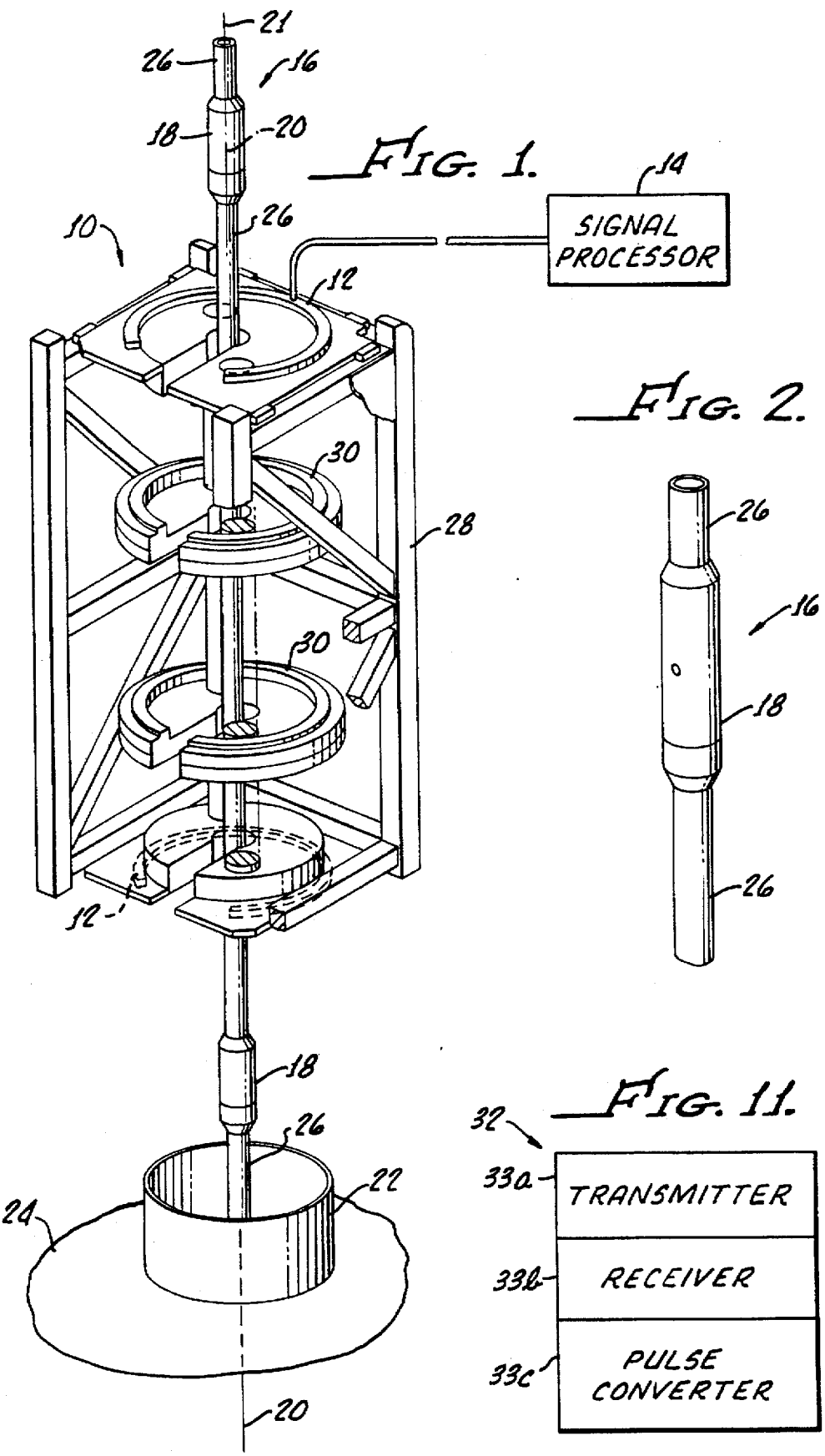

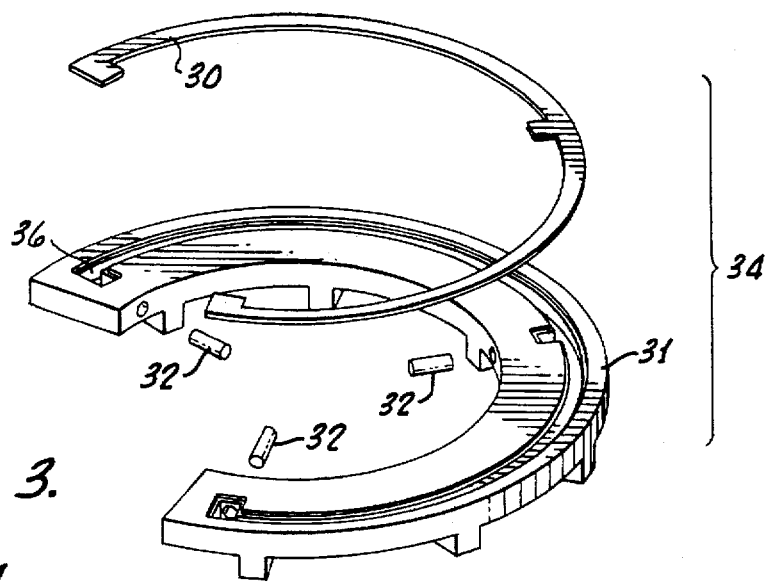
Fig. 3.
Fig. 4.
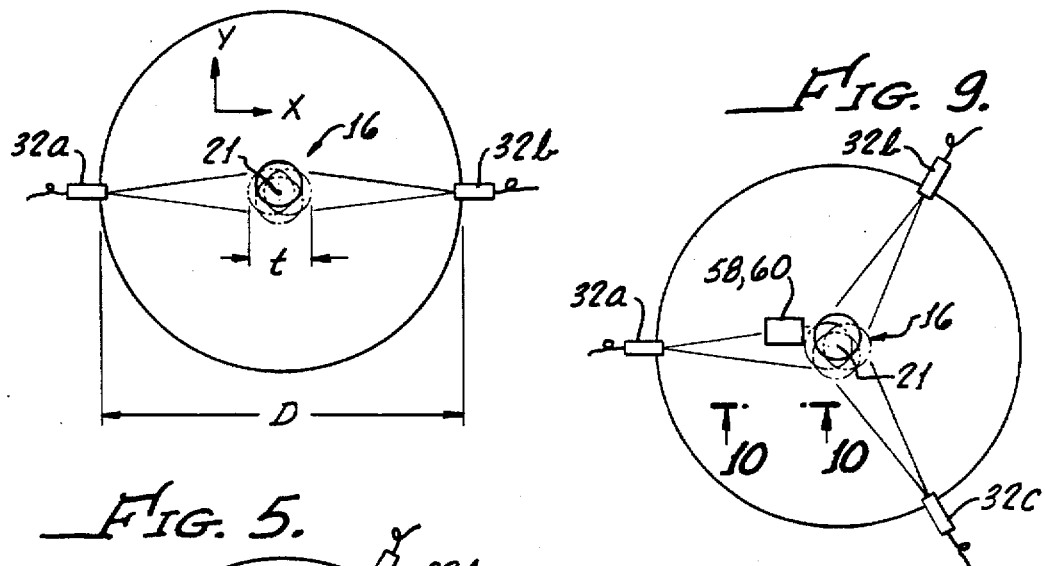
Fig. 9.
Fig. 5.
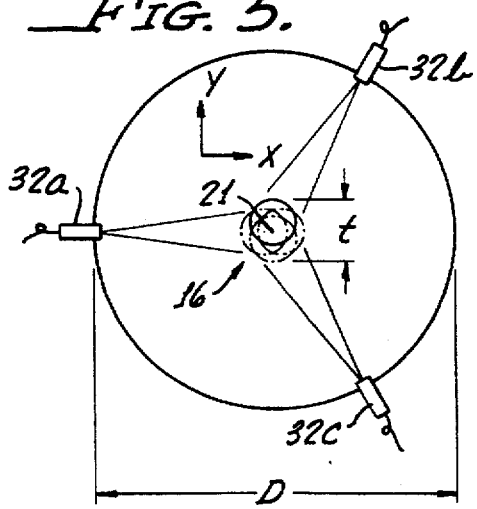
Fig. 10.

TOOL JOINT SENSOR

BACKGROUND OF THE INVENTION

1. Field of the Invention

The present invention relates generally to apparatus and methods for detecting or gauging objects located at a significant distance from the detecting or gauging apparatus and more particularly concerns ultrasonic sensing of transverse dimensional changes along the length of a rotating tool subject to random transverse displacement.

2. Description of Related Art

The detection and measurement of small changes in surface dimensions for a moving object is an important task in a variety of manufacturing, operational and testing fields. Where fabrication of parts on a production assembly or operating line involves monitoring of surface conditions, or where proper operation of a moving tool depends on continual sensing of the shape of the tool, traditional sensing methods have been employed with mixed success dependent on the size, movements of the part or tool, and ambient conditions.

For example, in the field of exploring for and extracting subterranean commodities such as oil and gas, continuous measurement of diameter changes along the length of a rotating drill pipe is complicated by distortions due to random lateral displacement of the pipe. Moreover, lateral motion, i.e., continuing transverse displacement of the tool from its axis of rotation, coupled with the normal rotational movement, present a danger of injury to a measurement device that is positioned too close to the object to be measured and this discourages use of contact sensors and closely positioned sensors. Additionally, ambient conditions interfere with some types of sensors or make their use totally impractical.

Preferably, a sensing device for such drilling operations would have the capability of precise gauging (on the order of 0.1"), correct for random traverse motion, be positionable at a safe distance from the object in motion, and overcome hostile environmental factors. Contact sensors, such as the line of gauges from Ono Sokki of Illinois, may meet the precision criterion and are relatively unaffected by the environment, but are subject to physical weardown from continuous contact and will most likely sustain proximity damage from lateral tool motion. Similarly, capacitive and inductive sensors, such as supplied by Baumer Electric of Southington, Conn. or Gordon Products of Brookfield, Conn. provide excellent precision, but are strained to accommodate the expected transverse motion and must be located undesirably and dangerously close (within 6") to the moving object. Finally, optical sensors including those supplied by Acuity Research of Cupertino, Calif. have sufficient precision and may be positioned out of danger from rotational or transverse motion, but they cannot cope with the mud, high temperatures, corrosive fluids or other environmental conditions typical of drilling sites.

Accordingly, it is an object of the present invention to provide detecting and measuring of a moving tool that avoids or minimizes problems including those mentioned above.

SUMMARY OF THE INVENTION

In carrying out principles of the present invention in accordance with the preferred embodiment, a tool joint sensor apparatus detects the location of a joint in a moving drilling tool by scanning the tool to detect changes in the thickness of the tool using the summation of outputs from ultrasonic sensors operating at a significant distance from the outer surface of the tool.

A combination of ultrasonic sensors, or a single sensor with an acoustic reflector, are arranged to provide pulses reflected from more than one area of the tool. Each reflected pulse is converted to an electrical output signal indicative of the distance between the transmitting sensor and the outside surface of the tool. Distance distortions in any individual reflected pulse caused by random transverse motion of the tool are corrected for by summing the respective output signals, thereby eliminating components of transverse axial motion in opposing directions and increasing signal to noise ratio. The summed output signals are then compared with a detection threshold voltage determined by the predetermined widest (joint) and narrowest (pipe) extremes of tool diameter. Whenever the summed output signal falls below the detection threshold voltage, i.e., when the distance from sensor to tool surface is sufficiently small enough to denote presence of a joint, a detection output pulse is generated.

According to another feature of the present invention, the summed output signal is also compared with a failure reference voltage to detect failure of a sensor. The failure reference voltage is set approximately midway between the value of a summed output signal from a fully functional sensor array and the value of summed output signal from an array with one failed sensor.

According to another feature of the present invention, variations in the speed of sound due to temperature and humidity are compensated for by reflecting a portion of a sensor ultrasonic beam back as a pulse from a reflecting target positioned at a known distance from the transmitting sensor. The target pulse is then compared with the tool pulse to correct for the then existing speed of sound.

BRIEF DESCRIPTION OF THE DRAWINGS

FIG. 1 is a pictorial view of a tool and tool joint detection apparatus mounted on a tool drive structure and embodying the principles of the present invention.

FIG. 2 is an enlarged perspective view of a joint portion and pipe portion of the tool of FIG. 1.

FIG. 3 is an exploded perspective view illustrating a three-sensor arrangement of the ultrasonic sensor assembly of FIG. 1.

FIG. 4 is a diagrammatic plan view illustrating a two-sensor arrangement of the ultrasonic assembly of FIG. 1.

FIG. 5 is a diagrammatic plan view of the ultrasonic sensor assembly of FIG. 3.

FIG. 9 is a diagrammatic plan view of a three-sensor assembly illustrating the position of a calibrating mirror within an ultrasonic sensor beam of FIG. 5.

FIG. 10 is a diagrammatic side view of the mirror of FIG. 9 illustrating employment of a planar reflector to extend a calibration path.

FIG. 11 is a functional block diagram illustrating three component functions of an ultrasonic sensor employed in the present invention.

DETAILED DESCRIPTION OF AN EXEMPLARY EMBODIMENT

Figure 6:
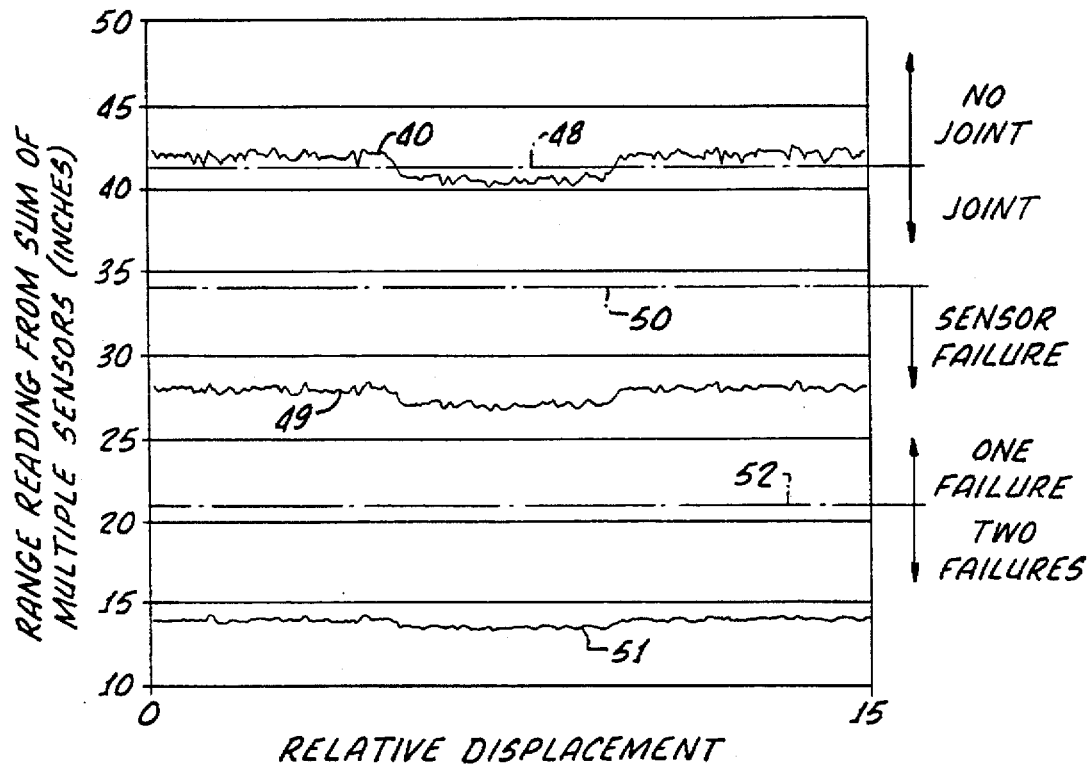
FIG. 6 illustrates a graphical summation of outputs of the three-sensor assembly of FIGS. 3 and 5 with various numbers of failed sensors.

An apparatus 10 including an ultrasonic sensor assembly 12 and signal processor 14 embodying the features of the present invention is illustrated in FIG. 1. A drilling tool 16 having a number of tool joints 18 descends (forward) or ascends (reverse) along an axis 20 of a fixedly positioned drilling enclosure 22 projecting downward from a drill floor 24. The elongated drilling tool is rotated about axis 20 as it is axially driven downwardly or upwardly. It is formed of a number of drill pipe sections connected in end to end relation at tool joints 18. The tool 21 axis nominally coincides with enclosure axis 20 but the long flexible pipe string is laterally displaced from enclosure axis 20 to varying extents as it is driven or pulled.

A typical tool joint in drilling tool 16 is shown in more detail in FIG. 2. For a 3.5 to 6.625" diameter drive pipe, for example, tool joint portion 18 is in the range of 1" to 2½" larger in outside diameter than is a pipe portion 26 and the tool joints are located generally 30 feet apart on drilling tool 16. Drilling tool 16 may be rotated by a variety of pipe rotating devices, one of which is a FloorDrive™ structure 28 available commercially from Paul-Munroe Engineering having C-shaped grippers 30 which must grip the drilling tool 16 at pipe portions 26 thereof, between the joints, to prevent damage to tool joints 18. Grippers 30 are shaped and sized to fit the diameter of pipe portions 26 and must be effectively kept from engaging drilling tool 16 at the larger diameter joint portion 18.

Therefore, to provide information to a gripper controller (not shown) for aligning pipe portions 26 with grippers 30 and to assure that the grippers 30 only grip the pipe portion and not the tool joints, the ultrasonic sensor assembly 12 of this invention is mounted in a plane perpendicular to drilling tool 16 on a non-rotating platform of PME FloorDrive™ structure 28 and is connected electronically to a signal processor 14 for generating a detection pulse as input to a gripper controller (not shown) when each tool joint 18 enters the plane of sensor assembly 12. One sensor assembly 12 is positioned upon the upper platform of floor drive structure 28 for sensing tool joints 18 during forward or downward advancement of tool 16. Another sensor assembly 12 is located beneath the lower platform of floor drive 28 to detect tool joints 18 when tool 16 is ascending, i.e., in the reverse direction. The detection pulse inhibits the grippers 30 from closing upon tool 16 for a time interval equal to the time during which tool join 18 is in the plane of the sensor assembly. Actual inhibiting of grippers 30 is delayed to compensate for the distance of tool 16 travel between the plane of sensor assembly 12 and the closest approach of gripper 30 to the sensor assembly plane.

The placement of ultrasonic sensors 32 in sensor assembly 12 for a three-sensor embodiment is illustrated in FIG. 3. A typical sensor 32 may be, for example, one of the RPS line supplied by Migatron Corporation of Woodstock, Ill. This sensor includes a transmitter 33a illustrated in the block diagram of FIG. 11 that generates an ultrasonic beam directed toward a remote object, a receiver 33b that receives a reflection of the transmitted beam as a pulse, and a pulse converter 33c that produces a output signal indicative of the distance between the sensor and the remote object from which the generated ultrasonic energy beam is reflected. Sensors 32 are spaced around and fixedly mounted to the inner diameter of a flat C-shaped mounting ring 34. Transmitter ultrasonic beams are directed radially toward the center of the ring. Output signals from each sensor 32 are transmitted to signal processor 14, (FIG. 1) via conductors channeled within a cable cavity 36 and protected by a cable cover 30. A typical sensor mounting ring 34 has an inner diameter of approximately 32 inches corresponding to the diameter of drilling enclosure 22, and an outer diameter of 48 inches. Since drilling tool 16 may have diameters ranging from 3½" to 9⅛", it will be appreciated that sensors 32 are safely positioned and operating at a substantial distance from the rotating tool 16, generally 12 inches or more. A significant separation between sensor 32 and drilling tool 16 is important also to eliminate injury to the sensors due to random transverse motion which may be as great as on the order of ¾" displacement of drilling tool 16.

As previously discussed, the detection of a tool joint 18, i.e., an increase in the diameter of tool 16, is achieved by monitoring and measuring the distance from a sensor 32 to the exterior of tool 16 as the tool is axially moved past the sensor. A disadvantage of such a method is that unavoidable transverse displacement of the tool will introduce errors in tool diameter measurement. This is because the effective distance from sensor to tool exterior will fluctuate unavoidably with the transverse displacement of the tool. However, components of transverse displacement are canceled by the multiple pulse method of this invention, as explained below.

The concept of measuring changes in diameter of the drilling tool 16 under conditions of random transverse displacement of the tool can be described by referring to FIG. 4. To simplify the explanation of the fundamental measurement process, two sensors 32 are employed in the baseline arrangement of FIG. 4. FIG. 4 schematically represents two sensors mutually and diametrically opposed on opposite points of the circumference of a circle of diameter D corresponding to the diameter of pipe enclosure 22 and having a center 21 as the normal tool axis. The diameter of tool 16 in the plane of the circle is t, and the orthogonal components of the random displacement of tool 16 from the center of the circle are represented by x, y. Ultrasonic echo ranging measurements of the distance between the left or right sensor on the circumference of the circle and the outside of the tool 16 are distorted by the component of tool random transverse motion (x) on the line of a diameter between the two sensors. The illustration of tool 16 in FIGS. 4, 5, 6 and 9 represents a stylized view of transverse tool displacements in several coplanar directions. As is obvious by inspection, there is no y- component of tool motion along this diameter line. Therefore, displacement in the y direction has no effect on this discussion of FIG. 4 which describes measurement along a single axis. Additional inaccuracy that is introduced in the output signal of a sensor is represented by a noise factor n, typically on the order of 0.1" for an individual sensor.

The output of the echo ranging sensor 32 is a signal having a magnitude indicative of or actually proportional to the distance between a point fixed on the sensor and an external object from which the sensor energy beam is reflected. As can be seen from a consideration of FIG. 4, the output of either sensor (distance to the surface of the tool 16) is the distance R from the circumference to the center 21 of the circle minus the radius t/2 of the tool 16, all adjusted by (a) the in-line displacement x of the tool 16 due to random motion (additive for one sensor, subtractive at the same moment in time for the other sensor), and (b) the noise measurement n characteristic of each sensor. If the output distance and noise measurements for the left sensor 32a are designated "$R_1$" and "$n_1$", respectively, and the diameter of the tool 16 is "t", then for a positive x displacement (toward the right as seen in FIG. 4) the above analysis may be given as $$R_1 = D/2 - t/2 + x + n_1. \qquad \text{Eq.(1)}$$

Similarly for the right sensor 32b, $$R_2 = D/2 - t/2 - x + n_2. \quad \text{Eq.(2)}$$

Summing the two outputs to establish the total diameter of the tool 16, $$R_1 + R_2 = D - t + RSS(n_1, n_2) \quad \text{Eq.(3)}$$

where RSS is the root sum square of the individual random noises in the measurement. Since D is a known constant, the tool diameter t at any longitudinal point and with any unknown random transverse displacement is uniquely determined within the noise uncertainty. Transverse displacement has been eliminated from the measurement. In other words, the sum of $R_1$ and $R_2$ is constant even though $R_1$ and $R_2$ individually vary due to the axis displacement.

The simplified arrangement of FIG. 4 is useful to explain principles of the present invention, and need not account for any y component of the random transverse displacement of the drill string. This is because each sensor beam has a beam width that is broad enough to encompass any potential lateral (y-axis) movement of pipe 16, and is centered along a single line (x-axis) between the sensors so that only the x-component of transverse motion is significant. That is, each sensor beam is divergent, with an included angle in this case of about 8°.

An alternative embodiment providing further redundancy and improved detection probability is illustrated in the three-sensor schematic of FIG. 5, corresponding to the sensor assembly of FIG. 3. This arrangement includes three sensors, 32a, 32b, 32c equally spaced circumferentially around the center 21 which is the nominal center of the drill string. In this arrangement all x and y components of random transverse displacement in all radial directions of the drill string are significant but are eliminated from the measurement as follows.

Sensor 32a is directly analogous to the left sensor of FIG. 4, and its output is therefore taken without further development from equation (1) as $$R_a = D/2 - t/2 + x + n_a \quad \text{Eq.(4)}$$

where $R_a$ is the distance measured by sensor 32a and $n_a$ is the noise of sensor 32a.

However, the beams from sensors 32b and 32c are not colinear with either the x-component or the y-component of random motion of drilling tool 16. With respect to sensor 32b, its placement 120° from sensor 32a results in an angle of (120°−90°)=30° from the y-direction so that the y-component of motion in the direction of sensor 32b is y cos 30° toward sensor 32b, i.e., subtractive from the distance to the sensor 32b. Similarly, the x-component of motion toward sensor 32b is x cos 60°. The output $R_b$ of sensor 32b is therefore represented by $$R_b = D/2 - t/2 - x \cos 60° - y \cos 30° + n_b \quad \text{Eq. (5)}$$
$$= (D - t)/2 - .5x - .87y + n_b \quad \text{Eq. (6)}$$

In like manner, since the y-component of motion is away from sensor 32c, i.e., additive to the distance from sensor 32c, $$R_c = D/2 - t/2 - x \cos 60° + y \cos 30° + n_c \quad \text{Eq. (7)}$$
$$= (D - t)/2 - .5x + .87y + n_b \quad \text{Eq. (8)}$$

Summing the outputs as in the base line analysis above, $$R_a + R_b + R_c = 3/2 (D-t) + RSS(n_a, n_b, n_c). \quad \text{Eq.(9)}$$

As in the baseline analysis, tool 16 diameter t is uniquely determined here as well. Compared with the baseline embodiment, the three-sensor embodiment has the advantages of higher signal to noise ratio. In addition, when used with the signal processor 14 arrangement in conjunction with FIGS. 6 and 7, it permits determination of failed sensors as will be described below.

An illustration of sensor array output for the summation of three sensors is shown as a plot of range readings versus displacement along the tool length in FIG. 6. For a nominal radial distance of 14" from sensor 32 to pipe 36 surface (no joint), the summed output 40 from three functioning sensors 32 is seen to hover generally about a value of 42" representing three times the individual (14") readings. As a joint 18 having a 0.5" increase in radius, appears, there is a decrease in the summation of the three ranges equivalent to three times the joint radius increase, or 1.5". By placing a threshold voltage 48 at the half-way point of the decrease, (approximately 41"+), and comparing the summed sensor output to this threshold, joint 18 is detected reliably even in the presence of expected sensor noise shown as the variation about the nominal summed output 40. Detection probabilities can be improved by employing known sampling techniques which require a multiplicity of values below detection threshold 48 before declaring that a joint 18 is detected.

FIG. 6 also illustrates the conditions resulting from the failure to zero, the expected failure mode, of one or more sensors 32. Since the summation of the two remaining functioning sensors 32 will have a value 49 wavering about 28", a sensor failure reference voltage 50 set generally equidistantly between 28" and 41", say, at 34", will positively detect the failure of one or more sensors 32 by comparing the summed output with this lower threshold to show the output well below the lowered threshold when one (or more) sensors have failed. Similarly, if no more than one sensor 32 falls to zero, the output will not fall to 14". A one-sensor failure threshold voltage 52 thus is set at approximately 21" to determine whether only one sensor (sum 49 above voltage 52) or more than one (sum 51 below voltage 52) has failed.

Figure 7:
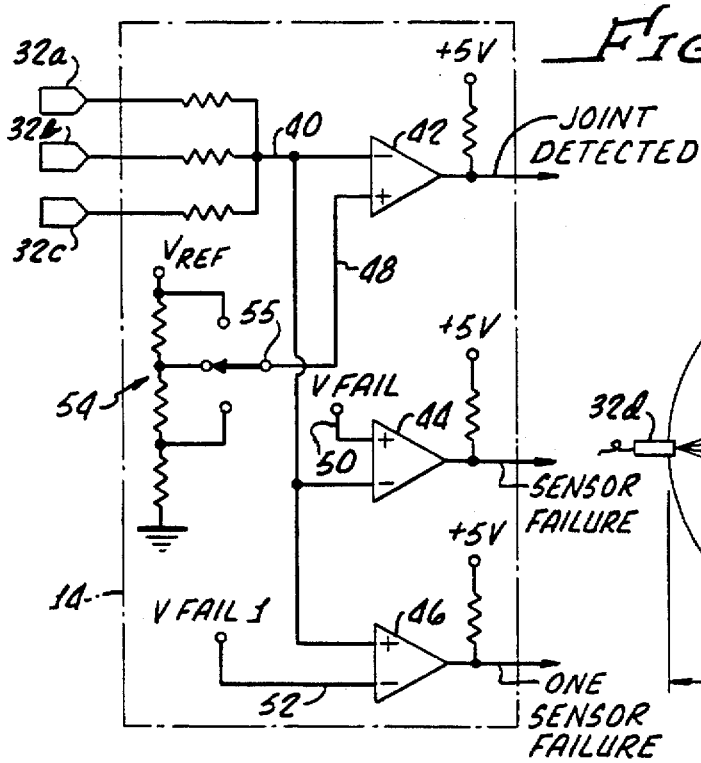
FIG. 7 is a schematic diagram of electronic components employed to generate detection and failure signals for the three-sensor output summations of FIG. 6.

Exemplary circuitry of the signal processor 14 for detecting both the presence of a joint 18 and failure of one or more sensors 32 is illustrated in FIG. 7. Individual outputs from the three sensors 32a, 32b, 32c are summed and the summed output 40 is fed into the negative input terminals of a joint differential comparator amplifier (comparator) 42 and of a sensor failure differential comparator amplifier 44. Summed output 40 is also fed into the positive input terminal of one-sensor failure differential comparator amplifier 46.

With reference to joint comparator 42, detector threshold voltage 48 is generated by a resistor voltage divider tree 54 based on the known diameters of the pipe 26 and joint 18 to be detected, and is fed into the positive input terminal of joint comparator amplifier 42. Resistor voltage divider 54 is shown for conceptual purposes as providing threshold level 48 via a switch 55. However, detection threshold voltage 48 may instead be provided by a computer controlled level produced as known in the art. The sensor failure threshold levels 50 ($V_{FAIL}$) and 52 ($V_{FAIL1}$) remain unchanged for a wide range of pipe and joint diameters, and may be provided by a voltage supply source known to one of ordinary skill in electrical design.

When the summed sensor output 40 is less than detector threshold voltage 48, the output of joint comparator 42 will be a logic "HIGH" or "ON" voltage signalling the presence of a joint 18 to a gripper controller or other device (not shown). Comparator 42 will have a logic low or "OFF" output as long as summed sensor output 40 remains greater than detector threshold voltage 48, declaring the "pipe" or "no-joint" condition. The output signals from sensor failure comparators 44, 46 may be represented in a variety of forms, including lamps in an indicator panel, voltage to trigger shutdown of operations, or combinations thereof.

Referring now to sensor failure comparator 44, the summed sensor output is compared with sensor failure reference voltage 50 (determined as previously discussed). If summed output 40 falls below sensor failure reference 50, the high ("ON") output of sensor failure comparator 44 declares that one or more sensors have failed, and operations should stop.

If one and only one sensor 32 has failed, one-sensor failure comparator 46 indicates this condition as follows. As long as summed sensor output 40 remains above one-sensor failure reference voltage 52, then the output from one-sensor failure comparator 46 will be at a logic high (ON) level, indicating that at least some sensors are generating output voltages. However, if sensor failure comparator 44 is also "ON" at the same time, the two "ON" indicators together announce that only one sensor has failed. When summed output 40 is below reference voltage 52, comparator 44 is still ON, but comparator 46 is now OFF, indicating that two or more sensors 32 have failed.

An additional comparator (not shown) could be used in like manner to determine whether two and only two sensors have failed if that were necessary. Additionally, although failure to zero is the expected sensor mode, sensor logic could be arranged to present less than total failure as a zero output, assuring the "expected" failure mode. Alternatively, logic could be included in signal processor 14 to vary the failure output combinations or to provide different results upon less than total failure of any one sensor.

Figure 8:
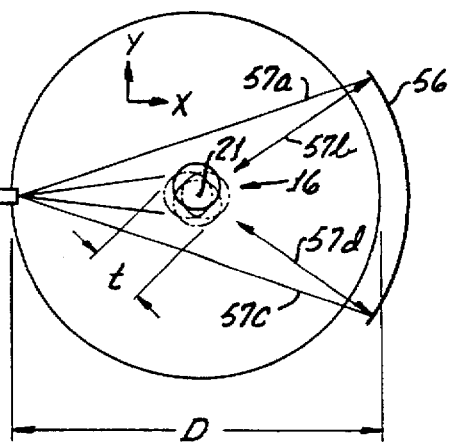
FIG. 8 is a diagrammatic plan view of a single-sensor embodiment of the present invention.

An embodiment that employs a single sensor 32 is illustrated in FIG. 8. Sensor 32d, also fixedly mounted on structure 28 as are all of the above described sensors, transmits an ultrasonic beam having a width of about 16°, approximately twice as wide as the beam transmitted by the sensors in the multi-sensor embodiments discussed above, outer portions of the beam on both sides of the tool are not impeded by the tool in any extreme position of tool random lateral displacement. A central portion of the beam impinges upon the tool 16 and is reflected in a first (direct) pulse as previously described. Energy from one outer portion of this wider beam propagates around tool 16 along a first indirect path leg 57a and is reflected along leg 57b from an ultrasonic reflector 56, preferably parabolic in shape, that is fixedly mounted to structure 28 to receive a part of the energy beam emitted by the transducer. The energy is reflected back between the reflector and tool along path leg 57b and finally returns as a second (indirect) pulse along path leg 57a back to the sensor 32. In a similar manner, the other outer portion of the beam travels out along legs 57c and 57d, and is reflected back along 57d and 57c. Sensor ring diameter D, tool diameter t and tool transverse axial motion components x and y are defined as before. The first (direct) pulse magnitude i.e., the component of sensor output caused by the first pulse $P_1$ is given by the relation described above in Eq. (1).

$$p_1=(D-t)/2+x+n_1 \quad \text{Eq.(10)}$$

where $n_1$ is the noise in the measurement of sensor 32d and the second (indirect) pulse with the two components along paths 57a–57b and 57c–57d is given by $$p_2=(3D-t)/2-x+n_2 \quad \text{Eq.(11)}$$

where $n_2$ is the noise in the measurement for the indirect path 57a through 57d. Summing the two pulses, $$p_1+p_2=2D-t+RSS(n_1,n_2), \quad \text{Eq.(12)}$$

once again providing an output independent of the transverse motion components of the tool 16. The single sensor concept of FIG. 8 minimizes the number of sensors yet, through the summing process, increases signal to noise ratio for detection.

It can be shown that the speed of sound increases with increasing ambient temperature and also with increasing humidity. Accordingly, it is highly desirable to compensate for the variations in the speed of sound that will affect ultrasonic ranging measurements caused by the temperature and humidity conditions encountered in whatever field the present invention is utilized. Temperature changes on the order of 20° F. could introduce unacceptably large measurement error, as could humidity changes of as little as 50%, both well within expectable field limits. Although temperature and humidity sensors capable of satisfactory measurement corrections are available, their cost and complexity of feedback tend to render their use undesirable.

However, another approach to compensating for variations in the speed of sound is to calibrate its value by comparing travel times of two pulses at the time of each transmitted beam. This may be accomplished by modifying the single sensor concept of FIG. 8 to employ a wider beam and planar reflector at a known distance on the other side of tool 16 from the sensor 32, to produce a third pulse from the reflector for calibrating as explained below. To overcome the problems of access, size of apparatus and lack of redundancy inherent in the single sensor concept, a preferred calibration arrangement utilizing the three-sensor concept is now described with reference to FIG. 9.

An acoustic mirror 58 is positioned at a fixed location in the path of one sensor 32a and intercepts an outer portion of its beam. The remainder of the beam impinges on the tool and is reflected back to the sensor as described above. The size of the intercepted portion is chosen to provide a real time calibration pulse while at the same time maintaining sufficient beam energy to reflect from tool 16 for contributing to the pulse-summing processes described above. Intercepting a beam portion in the order of 10% to 25% of beam width is acceptable for accomplishing speed of sound calibration without adversely affecting the ultrasonic ranging function of sensor 32.

Real time calibration of the speed of sound is achieved in the following manner. Ultrasonic sensor 32 measures the round-trip time for an ultrasonic beam impinging on tool 16 and travelling back to the sensor as a reflected pulse. The range to the tool 16 is the round-trip time t (divided by 2) times the speed of sound $C_s$, or $R=\Delta t/2C_s$.

To account for variations in the speed of sound due to temperature and humidity changes, the calibration target is placed in the sensor beam at a fixed distance ($R_m$) from the sensor. The beam has an associated round-trip time of flight to the calibration target ($\Delta t_m$) so that $R_m=\Delta t_m/2C_s$. Correspondingly, the range to tool 16 ($R_a$) is $R_a=\Delta t_a/2C_s$, where $\Delta t_a$ is the time of flight to the tool. The range to tool 16 ($R_a$) may then be expressed as $$R_a=(\Delta t_a/\Delta t_m)R_m. \quad \text{Eq.(13)}$$

Since $R_m$ is a known constant, and the ratio of $\Delta t_a$ to $\Delta t_m$ is easily determined, $R_a$ is effectively corrected for variations in the speed of sound. However, since the value of $R_a$ is affected by individual sensor accuracies, the corrected variance $\sigma^2_{Rac}$ is given by $$\sigma^2_{Rac} = \sigma^2_{Ra}(1+(R_a/R_m)^2)x \qquad \text{Eq.(14)}$$

where $\sigma^2_{Ra}$ is the uncorrected variance in $R_a$

In other words, the variance of the corrected range estimate is increased by the correction. For example, if the distance $R_m$ to the calibration target were equal to the distance to tool 16, ($R_a=R_m$), the variance would be twice the uncorrected variance. $\sigma^2_{Rac} = \sigma^2_{Ra}(1+1) = 2\sigma^2_{Ra}$, the standard deviation would increase by 41% and the rms single sensor noise would be 0.14" instead of 0.1". Decreasing the calibration target distance to a more physically practical distance closer to the sensor, say, half-way, where $R_M=R_a/2$, would worsen the variance, i.e., $$\sigma^2_{Rac} = \sigma^2_{Ra}(1+(R_a/R_a/2)^2) = 5\sigma^2_{Ra} \qquad \text{Eq.(15)}$$

It is clear that a calibration distance $R_m$ larger than $R_a$ is desirable. Of course, as $R_m$ increases absolutely, less energy is available in the calibration portion of the beam for reflecting back to the sensor. An acceptable compromise occurs when the calibration distance is double that of the tool distance $R_a$. If, for example, $R_m=2R_a$, the variance increases by only 25%, and the standard deviation of 12% results in a displacement noise measurement of only 0.11" i.e., almost no degradation with sufficient reflective energy.

Although placing an acoustic mirror in a beam path at or beyond the tool distance is physically impractical, the extended calibration path can be achieved by "folding" the calibration path as illustrated in FIG. 10. Acoustic mirror 58 is positioned to intercept the beam from sensor 32a a short distance from sensor 32a at the end of a rod or other mounting arm (not shown) fixedly carried by mounting ring 34. The arm preferably extends radially outward from sensor 32 so that mirror 58 is generally perpendicular to an outer edge of a sensor 32 ultrasonic beam. Mirror 58 is then angled to deflect the intercepted path of the beam upward or downward toward a planar reflector 60 (FIG. 10) to lengthen the effective total travel of the calibration path with minimal length along a diameter of sensor assembly 12.

Referring to FIG. 10, the total one-way travel $R_m$ of the calibration path is the sum of the distance from sensor 32a to calibration mirror 58 ($R_{m1}$) plus the distance from mirror 58 to reflector 60 ($R_{m2}$). Thus, $R_m=(R_{m1}+R_{m2})=2R_a$. Mirror 58 and reflector 60 are arranged so that the calibration energy retraces its path back to sensor 32a, with the mirror and reflector combination physically occupying very little of the space surrounding tool 16.

There have been described apparatus and methods for detecting the presence of small increases in the diameter of a rotating and axially advancing object, subject to transverse motion, without making physical contact with the object. The apparatus of this invention provides accurate gauging of a remote object by overcoming movement errors introduced by random or otherwise unknown lateral motion on vibration of the object. Employing ultrasonic sensors achieves the objective of safeguarding the gauging device from damage due to proximity to the moving object to be measured, and errors in ultrasonic measurement arising from temperature and humidity conditions are also minimized by a feature of this invention. The foregoing detailed description is to be clearly understood as given by way of illustration or example only, the spirit and scope of this invention being limited solely by the appended claims.

What is claimed is:

1. A method of detecting a joint in an elongated rotational and axially movable tool having a nominal axis, wherein the joint has a diameter different from the diameter of the tool at portions of the tool other than the joint, said method comprising the steps of:

employing at least one divergent ultrasonic energy beam to measure at least first and second distances between circumferentially spaced points on the exterior of the tool and at least one point positioned at a fixed radial distance from said nominal axis, wherein said circumferentially spaced points lie in a common plane; and employing said at least first and second measured distances to determine diameter of said tool in said plane; and using the diameter difference between the joint and the portions of the tool other than the joint to detect when the joint passes into said common plane.

2. The method of claim 1 including the step of causing said elongated tool to move axially of said common plane while measuring said at least first and second distances.

3. The method of claim 1 wherein the tool is subject to an unknown transverse displacement and further including the steps of disposing said circumferentially spaced points diametrically opposite to one another on said tool, and summing said at least first and second measured distances to minimize measurement errors due to said transverse displacement.

4. The method of claim 1 wherein said step of employing at least one divergent ultrasonic energy beam comprises steps of: positioning at least first and second ultrasonic energy beam transmitting/receiving devices at mutually angularly spaced positions around and at fixed radial distances from said nominal axis, receiving at said ultrasonic energy beam transmitting/receiving devices energy pulses reflected from said tool, and providing first and second outputs from said ultrasonic energy beam transmitting/ receiving devices respectively representing said at least first and second distances between points on said tool and said devices, and combining said first and second outputs.

5. The method of claim 1 wherein said step of employing at least one divergent ultrasonic energy beam comprises steps of: positioning a single ultrasonic energy beam transmitting/receiving device at a radial distance from said nominal axis, positioning a curved reflector at a position opposite said ultrasonic energy beam transmitting/receiving device, employing said ultrasonic energy beam transmitting/ receiving device to measure one of said at least first and second distances along a first path that extends directly between said ultrasonic energy beam transmitting/receiving device and said tool, and to measure the other of said at least first and second distances along a second path having sections extending between said ultrasonic energy beam transmitting/receiving device and said curved reflector and between said tool and said curved reflector, and summing said at least first and second distances.

6. A method of detecting and measuring changes in the outside diameter of a tool having a nominal axis, and which tool is subject to unknown transverse displacement from said nominal axis, said method comprising the steps of:

providing an ultrasonic sensor assembly generating at least one divergent transmitted pulse and receiving a plurality of substantially contemporaneous reflected pulses from said tool, for which the flight times of said reflected pulses are representative of the diameter of said tool, said ultrasonic sensor assembly having at least one ultrasonic sensor transmitting a divergent ultrasonic pulse toward said axis;

positioning said ultrasonic sensor assembly to coaxially encircle said nominal axis in a plane perpendicular thereto;

scanning said tool by directing multiple ones of said divergent ultrasonic pulses at said tool while said tool is in axial motion relative to said sensor assembly;

reflecting a portion of each of said multiple ones of said divergent ultrasonic pulses from an outer surface of said tool to provide a plurality of substantially contemporaneous reflected pulses from said tool;

converting each of said plurality of substantially contemporaneous reflected pulses to a corresponding respective electrical output signal;

summing said electrical output signals to produce a summed voltage for minimizing measurement error due to said unknown transverse displacement;

establishing a detection reference voltage; and comparing said summed voltage with said detection reference voltage to establish a threshold for generating a detection output pulse.

7. The method of claim 6 wherein the step of scanning said tool further comprises directing said divergent ultrasonic pulse at both said tool and at a curved reflector to produce respective ones of said plurality of substantially contemporaneous reflected pulses which are reflected directly from said tools and other ones of said plurality of substantially contemporaneous reflected pulses which are reflected indirectly from said reflector.

8. The method of claim 6 further comprising the step of employing said divergent pulse to measure the contemporaneous speed of sound under prevailing ambient conditions.

9. The method of claim 8 wherein the step of employing said divergent pulse to measure the speed of sound further comprises providing a reflecting target at a fixed distance from said at least one ultrasonic sensor for intercepting and reflecting a portion of said divergent pulse as a calibrating pulse; and comparing one of said plurality of pulses reflected from said tool with said calibrating pulse to establish the speed of sound.

10. Apparatus for detecting and measuring outside diameter of an elongate object having a diameter and a nominal axis and which is subject to random transverse displacements from said nominal axis, said transverse displacements having certain limits, said apparatus comprising:

an ultrasonic sensor assembly which is relatively axially movable with respect to said object, said ultrasonic sensor assembly generating a plurality of divergent ultrasonic pulses respective portions of which are reflected from said object and the flight times of said pulse portions are representative of the diameter of said object, said ultrasonic sensor assembly being configured and arranged to generate at least one divergent ultrasonic pulse of which at least a portion is directed at said object, and said ultrasonic sensor assembly further being configured to receive said plurality of reflected portions each reflected along a corresponding different path from said object, and means to provide an electronic output signal proportional to each of said plurality of reflected portions; and a signal processor responsive to said sensor assembly for summing said output signals to minimize distortion effects of said random transverse displacement.

11. The apparatus of claim 10 wherein said electronic output signal includes signal noise, and wherein said signal processor includes means for minimizing effects of said signal noise.

12. The apparatus of claim 10 wherein said apparatus is mounted in a drive structure having a longitudinal axis and said object comprises a drill pipe tool disposed along said drive structure axis, said tool including a drill pipe portion, and a tool joint portion having a larger outside diameter than that of said drill pipe portion, and wherein said drive structure includes means for rotatably advancing said drill pipe tool along said nominal axis thereof.

13. The apparatus of claim 12 wherein said ultrasonic sensor assembly further comprises a sensor mounting ring coaxially encircling said tool and having at least one sensor housing incorporated therein, and an ultrasonic sensor having means for generating said divergent ultrasonic pulse, said ultrasonic sensor being fixed in said housing at a predetermined distance from said nominal axis and in a plane perpendicular to said nominal axis.

14. The apparatus of claim 13 wherein said ultrasonic sensor assembly further comprises a first ultrasonic sensor and a second ultrasonic sensor mutually and diametrically mounted on opposite sides of said tool, and wherein said signal processor includes means for summing said electronic signal outputs of said first sensor and said second sensor to provide an indication of tool outside diameter.

15. The apparatus of claim 13 wherein said processor includes means for computing said tool outside diameter in accordance with the equation $$R_1 + R_2 = (D-t) + RSS(n_1, n_2)$$

where $R_1, R_2$ = the outputs of said first and second sensor, respectively $D/2$ = the distance between each said sensor and said nominal axis $t$ = said tool outside diameter $n_1, n_2$ = said output signal noise of respective ones of said sensors and RSS = root-sum-square of said signal noises.

16. The apparatus of claim 14 wherein each said sensor pulse has a width sufficiently broad to include both said outside diameter of said elongate object and said random transverse displacements within said certain displacement limits from said nominal axis.

17. The apparatus of claim 13 wherein said assembly further comprises three substantially identical ultrasonic sensors equally spaced around said mounting ring, and each providing a corresponding ultrasonic pulse, and wherein said tool outside diameter is represented by $$R_a + R_b + R_c = 1.5(D-t) + RSS(n_a, n_b, n_c)$$

where $R_a, R_b, R_c$ = respective outputs of corresponding ones of said three ultrasonic sensors $D/2$ = a predetermined coequal distance between each one of said three ultrasonic sensors and said nominal axis $t$ = said tool outside diameter $n_a, n_b, n_c$ = the corresponding output signal noise of the respective ones of said three ultrasonic sensors, and RSS = the root-sum-square of said signal noises.

18. The apparatus of claim 17 wherein each of said three sensor pulses has a width sufficiently broad to include both said outside diameter of said elongate object and said random transverse displacements within said certain displacement limits from said nominal axis of said tool.

19. The apparatus of claim 17 wherein said sensor assembly further comprises a reflection target disposed between one of said three sensors and said tool, said reflection target intercepting and reflecting a portion of said ultrasonic pulse from said one sensor back to said one sensor for calibrating variations in the speed of sound.

20. The apparatus of claim 13 wherein said mounting ring further comprises a single sensor transmitting said ultrasonic pulse to said tool for reflection from said tool back to said single sensor as a first direct pulse, and said sensor assembly includes a curved ultrasonic reflector disposed diametrically opposite said single sensor for reflecting energy from said ultrasonic pulse to a surface of said tool opposite said single sensor, said tool and said ultrasonic reflector reflecting a part of said pulse back to said single sensor as an second indirect pulse, and wherein said electronic output signal comprises a first output component derived from said first direct pulse reflected from direct impingement of said ultrasonic pulse on said tool and a second output component derived from said second indirect pulse.

21. The apparatus of claim 20 wherein said tool outside diameter is represented by $$p_1 + p_2 = 2D - t + RSS(n_1, n_2)$$

where $P_1$ = a first distance represented by said first direct pulse output component $P_2$ = a second distance represented by said second indirect pulse output component $D/2$ = said predetermined distance between said sensor and said nominal axis $t$ = said tool outside diameter $n_1, n_2$ = the output signal noise of respective ones of said first and second output components and RSS = the root-sum-square of said signal noises.

22. The apparatus of claim 20 wherein said sensor pulse has a width sufficiently broad enough to encompass both said tool, and additionally approximately twice said known displacement limits of said tool for propagating said ultrasonic pulse energy around said tool to said curved reflector.

23. The apparatus of claim 17 wherein said signal processor includes a joint detecting comparator for generating a detection output pulse upon detection of an increase in said tool diameter.

24. The apparatus of claim 23 wherein said signal processor further includes at least one failure comparator for indicating failure of at least one of said sensors.

25. The apparatus of claim 17 wherein said means for providing detection pulse output components includes a resistor tree for providing a reference voltage corresponding to said tool outside diameter.

* * * * *